(12) United States Patent
Susi

(10) Patent No.: US 7,404,809 B2
(45) Date of Patent: Jul. 29, 2008

(54) NON-MAGNETIC MEDICAL INFUSION DEVICE

(75) Inventor: Roger E. Susi, Winton Park, FL (US)

(73) Assignee: Iradimed Corporation, Winter Park, FL (US)

( * ) Notice: Subject to any disclaimer, the term of this patent is extended or adjusted under 35 U.S.C. 154(b) by 282 days.

(21) Appl. No.: 10/964,333

(22) Filed: Oct. 12, 2004

(65) Prior Publication Data

US 2006/0079758 A1  Apr. 13, 2006

(51) Int. Cl.
*A61M 37/00* (2006.01)
(52) U.S. Cl. ..................................................... 604/131
(58) Field of Classification Search ................. 600/420, 600/407, 410, 431, 432; 604/83, 131, 151, 604/148
See application file for complete search history.

(56) References Cited

U.S. PATENT DOCUMENTS

| | | | |
|---|---|---|---|
| 2,696,963 A * | 12/1954 | Shepherd ................ 248/229.15 |
| 4,564,812 A | 1/1986 | Van Dijk |
| 4,689,043 A | 8/1987 | Bisha |
| 4,798,590 A | 1/1989 | O'Leary |
| 4,857,048 A | 8/1989 | Simons et al. |
| 4,888,514 A | 12/1989 | Takahashi et al. |
| 5,021,700 A | 6/1991 | Takahashi et al. |
| 5,059,173 A * | 10/1991 | Sacco ........................... 604/80 |
| 5,130,619 A | 7/1992 | Izuno |
| 5,494,036 A | 2/1996 | Uber, III et al. |
| 5,522,799 A | 6/1996 | Furukawa |
| 5,553,619 A * | 9/1996 | Prince ........................ 600/420 |
| 5,563,464 A | 10/1996 | Okubu et al. |
| 5,713,856 A | 2/1998 | Eggers et al. |
| 5,770,181 A * | 6/1998 | Kirkland ................... 424/9.37 |
| 5,864,331 A | 1/1999 | Anand et al. |
| 5,967,484 A | 10/1999 | Morris |
| 6,052,614 A | 4/2000 | Morris et al. |
| 6,117,115 A | 9/2000 | Hill et al. |
| 6,198,285 B1 | 3/2001 | Kormos et al. |
| 6,213,723 B1 | 4/2001 | Danby et al. |

(Continued)

FOREIGN PATENT DOCUMENTS

DE    19714711 A1    10/1998

(Continued)

OTHER PUBLICATIONS

International Search Report for PCT Application No. PCT/US03/19334, Mar. 15, 2004.

(Continued)

*Primary Examiner*—Kevin C. Sirmons
*Assistant Examiner*—Elizabeth R MacNeill
(74) *Attorney, Agent, or Firm*—Knobbe Martens Olson & Bear LLP

(57) ABSTRACT

Liquid infusion apparatus includes non-magnetic materials in a pumping structure and drive motor therefor, and in a controller that supplies drive signals to the motor to facilitate convenient operation in intense magnetic fields without distorting the magnetic fields and without radiating objectionable radio-frequency interference. A non-MRI-compatible liquid infusion apparatus is temporarily replaced with MRI-compatible, non-magnetic liquid infusion apparatus without disconnecting patient from an installed intravenous infusion set to continue infusing liquid within the MRI environment.

13 Claims, 6 Drawing Sheets

U.S. PATENT DOCUMENTS

| | | |
|---|---|---|
| 6,213,738 B1 | 4/2001 | Danby et al. |
| 6,213,739 B1 | 4/2001 | Phallen et al. |
| 6,221,045 B1 * | 4/2001 | Duchon et al. ............. 604/151 |
| 6,230,041 B1 * | 5/2001 | Prince ........................ 600/420 |
| 6,240,311 B1 * | 5/2001 | Prince ........................ 600/420 |
| 6,243,600 B1 * | 6/2001 | Prince ........................ 600/420 |
| 6,316,862 B1 | 11/2001 | Nakata et al. |
| 6,418,337 B1 | 7/2002 | Torchia et al. |
| 6,463,318 B2 * | 10/2002 | Prince ........................ 600/420 |
| 6,503,221 B1 | 1/2003 | Briggs et al. |
| 6,641,562 B1 * | 11/2003 | Peterson .................... 604/141 |
| 6,643,537 B1 | 11/2003 | Zatezalo et al. |
| 6,659,978 B1 | 12/2003 | Kasuga et al. |
| 6,889,072 B2 * | 5/2005 | Prince ........................ 600/420 |
| 2002/0010397 A1 * | 1/2002 | Prince ........................ 600/420 |
| 2002/0115933 A1 | 8/2002 | Duchon et al. |
| 2002/0127114 A1 | 9/2002 | Barak |
| 2002/0165503 A1 | 11/2002 | Morris |
| 2003/0014035 A1 * | 1/2003 | Trombley et al. ........... 604/500 |
| 2003/0171670 A1 | 9/2003 | Gumb et al. |
| 2004/0030281 A1 | 2/2004 | Goble et al. |
| 2004/0176984 A1 | 9/2004 | White et al. |
| 2005/0256388 A1 | 11/2005 | Susi |
| 2006/0042633 A1 | 3/2006 | Bishop et al. |
| 2006/0079758 A1 | 4/2006 | Susi |
| 2006/0173412 A1 | 8/2006 | Susi |

FOREIGN PATENT DOCUMENTS

| | | |
|---|---|---|
| EP | 0 447 985 A | 9/1991 |
| EP | 0 602 635 A1 | 6/1994 |
| EP | 0 606 099 A2 | 7/1994 |
| JP | 7-178169 | 7/1995 |
| WO | WO 02/00276 | 1/2002 |
| WO | WO 03/105925 A2 | 12/2003 |

OTHER PUBLICATIONS

International Search Report for PCT Application No. PCT/US05/36641, Jun. 12, 2006.

International Search Report for PCT Application No. PCT/US0319334, Mar. 26, 2007.

Partial International Search Report for PCT Application No. PCT/US2006/043816, Apr. 25, 2007.

International Search Report for PCT Application No. PCT/US2006/043816, date of mailing Sep. 21, 2007.

* cited by examiner

NON-MAGNETIC MEDICAL INFUSION DEVICE

FIELD OF THE INVENTION

This invention relates to the field of liquid infusion apparatus and more specifically to such apparatus for operation during study within a Magnetic Resonance Imaging (MRI) system in which extraneous radio frequency (RF) signals and magnetic materials within the MRI's environment cause detrimental interference to the imaging process, upset the function of the infusion device, and present hazards to the patient.

BACKGROUND OF THE INVENTION

It is desirable to carefully control the intravenous (IV) administration of liquids to a patient. Conventional gravity IV solution delivery via commonly-available IV administration sets is typically not sufficiently accurate for the delivery of many types of fluids and drugs. Various positive displacement pumping devices have been developed for carefully controlling such IV administration. Some types of IV pumps control flow within a standard IV administration set via peristaltic (either linear or rotary) pumping schemes directly on the tubing of a conventional IV infusion set. Other types may incorporate a proprietary volumetric cassette, and still other types utilize a syringe-like device. However, there currently exists no IV controller capable of completely safe operation within a MRI suite wherein a considerable need exists for the controlled delivery of medicinal liquids. Frequently, patients scheduled for MRI examination arrive at the MRI suite with IV solutions being administered and controlled by devices which must be disconnected as the patient is moved into the suite where high magnetic fields are present and no outside RF interference can be tolerated.

The basic characteristics of an infusion pump involve the delivery of medicinal or nutritional liquids, over time, into the venous system of a living subject. Certain physical limitations regarding the delivery rate and pressure are elemental in IV liquid-infusion control. IV fluids are pumped at pressures typically in the range of 0.2 to 10 PSI. The infusion device should include detection of over-pressure and operational limits at not more than about 20 PSI. Flow ranges typical of IV pumps are from 0.1 to 2000 ml/hr. Such specifications for conventional IV infusion apparatus are quite different from the specifications for injector devices which are often used in radiologic settings, including MRI, for purposes of very rapid bolus injection of image-enhancing contrast agents. Such devices 'push' contrast agents at pressures up to 300 PSI and in very short periods of time in contrast to IV drug delivery systems. Contrast agents are solely for image enhancement and have no medicinal value in a patient.

The high magnetic field surrounding MRI systems can negatively affect the operation of various devices (including conventional IV control devices), especially those devices that are constructed with magnetic materials, and can seriously jeopardize a patient's safety as a result of devices utilizing magnetic materials that can be attracted at high velocity into the magnetic field of the MRI system where patient or attendant personnel are located.

Conventional devices for infusing liquids into a patient are typically small portable units often attached to an IV pole holding both the infusion device and associated liquids to be infused. Some of such devices utilize either stepper-type motors or simple DC motors which include magnetic materials for providing the mechanical power required to drive the pumping unit. Further, some form of electronic control unit receives the manual inputs of prescribed infusion rate settings, and controls the pumping unit to deliver the desired quantity of liquid over time. Such control unit may emit spurious radio frequency signals as a result of poor electrical design or insufficient shielding.

With the advent of MRI procedures for the imaging of internal body structures, very special requirements must be satisfied in the design of medical devices intended to be used within the MRI environment. MRI systems exploit the physical phenomenon of nuclear magnetic resonance (NMR) by which RF stimulation of atomic nuclei within an associated magnetic field results in the emission of a small RF 'spin echo' from the nucleus so stimulated. In the case of patient imaging, hydrogen nuclei bound with water are the usual targets for magnetic resonance at selected frequencies. Other molecules and compounds can also be selected for study, as in Nuclear Magnetic Spectroscopy, by choosing resonance specific magnetic field strengths and associated radio frequencies. For simplicity the typical hydrogen atom-based MRI image-acquisition process is referred to herein, but it should be recognized that the subject invention is equally useful in MRI spectrographic studies at a plurality of field strengths and frequencies.

The typical MRI system includes several components, as shown in FIG. 1. For example, the operator's console 25, 27 and various processing 37, display 29, 31 and radio frequency and magnetic gradient amplifying equipment 33, 35 are all located outside of the environment of the MRI scanning suite which must be configured to eliminate image-degrading radio frequency interference and field effects of metallic structures that can introduce field distortions and become safety hazards. The MRI scanning unit produces large magnetic and RF fields, and must be capable of receiving the extremely small RF nuclear 'echoes', and is therefore typically located within a shielded room 11. Such rooms greatly attenuate outside RF noise and may also provide some containment of the scanner's magnetic field.

However, certain devices are required to be placed in the scan room either to assist with care of the patient being imaged or for the use of attending staff. Of particular interest are those devices which must be placed in the scan room during the time of image acquisition when the patient is present and the magnetic fields are 'up' and RF reception of the tiny nuclear 'echoes' must be cleanly acquired. Electrically passive metallic items such as oxygen bottles or 'crash carts' present safety hazards to the patient due to their potential to be strongly attracted by the magnetic field of the scanner. Such items can be 'pulled' into the imaging volume where the patient is located, creating potential for serious injury or death. Additionally, great effort is made during the manufacture and installation of the scanner/magnet to assure that the lines of flux within the imaging volume are highly homogenous to assure that acquired images have minimal spatial distortion. Thus, devices formed of magnetic material that are positioned within the magnetic field of the scanner can introduce distortions into this homogeneous field and the resultant images. The level of hazard and the degree of field/image distortion due to magnetic materials depends upon the composition and location with respect to the imaging volume.

The hazards due to 'flying' objects can be controlled to some degree by the use of non-ferrous devices such as the aluminum oxygen bottle. Additionally, the gravitational weight of some devices or their rigid fixation in the scanning room may be sufficient to overcome the force of magnetic attraction on the ferrous mass of such devices toward the imaging volume. However, such devices with some ferrous mass, though inhibited from being pulled into the magnetic field, may nevertheless introduce inhomogeneity in the magnetic field. Distortions in the homogeneity of the magnetic field within the imaging volume must be kept at such a level as to be of minimal consequence to the operator reading the resultant image or data. And, the possibility of field distortion is proportionally increased as devices with metallic materials are positioned closer to the imaging volume, with the most critical position being near the center of the imaging volume, essentially where the patient is positioned. Additionally, because of the extremely low levels of RF signals produced by the target image nuclei, great care must be taken to assure that devices with active electronic circuits do not emit spurious RF signals as forms of electronic noise. Such noise can so degrade the signal-to-noise ratio of signals received by the MRI sensor coils and receivers that image resolution is reduced or rendered completely unreadable. Active circuits must be carefully shielded to assure that their RF emissions are extremely low at the specific frequencies of the imaging process. Conversely, it is possible through careful design, to place a source of RF energy for signal transmission, therapy, or the like, within the MRI environment, but such signals must be chosen to avoid the discreet Lamar frequencies unique to the particular magnetic field strength of a given MRI scanner, and must be of such high spectral purity as to coexist with the MRI without causing any deleterious effects. The intense magnetic fields produced by the MRI scanner can cause detrimental effects on the performance of common DC and stepper motors in devices needed within the MRI scanning room, to the point of making their control difficult or causing their complete failure.

For example, injectors of image-enhancing contrast agents are commonly required to inject such contrast agent during actual imaging acquisition, and such devices include motors that contain magnetic material and that must therefore be located at a sufficient distance to reduce interactive effects with the magnet of the MRI scanner for proper operation and safety. Controllers and consoles of electronics and displays that generate spurious RF signals are therefore located outside the MRI scan room to avoid interference with the sensitive RF receivers of the RF scanner.

Accordingly, it is desirable to provide a self-contained, MRI-compatible infusion pump for the relatively long term control and delivery of the various infusion solutions and drugs routinely delivered to a patient within the MRI environment during image acquisition. Such devices must not emit any significant RF emissions that might adversely affect image acquisition operation from within the MRI scan room and must not interact with the magnetic fields therein either to cause distortion of the field or to be influenced by these fields sufficiently to jeopardize reliable operation of such devices.

For various reasons, including cost, safety, convenience, and performance, it may be desirable to use the MRI-compatible pump only for short durations while the patient is in the MRI. In this case, the patient must be disconnected from a non-MRI-compatible pump and connected to the MRI-safe pump prior to the MRI, and later switched back. Switching a patient's IV set involves a health risk due to sterility concerns and a cost in medical personnel's time. Additionally, fluid may be wasted from a prescribed volume during the IV-switch procedure.

Therefore, it is also desirable to provide a method for substituting an MRI-compatible pump for a prior-connected, non-MRI-compatible pump for a short duration without removing the patient from the original IV set. The MRI-compatible pump may be connected in substitution for the original pump after the original pump is removed. The original pump may be similarly reconnected, and the MRI-compatible pump removed, after the MRI is complete. By easily interchanging pumps on the same IV set installed on a patient, the time and expense of interchanging pumps are minimized, and compromises of the sterility of an IV installation on a patient are minimized.

SUMMARY OF THE INVENTION

In accordance with the illustrated embodiment of the present invention a safe and effective infusion device for use within the MRI scan room achieves reduction of magnetic material and accurate pumping control as well as reduction of RF emissions. In one embodiment, the infusion device includes an ultrasonic motor that eliminates magnetic materials and that does not produce any detrimental magnetic fields and that is not affected by external magnetic fields. The ultrasonic motor drives a peristaltic or other suitable fluid pumping mechanism, and is driven by a multiphasic electronic signal specifically designed to produce very little RF harmonic noise in the spectral range of about 6 Mhz to 130 Mhz in which MRI receivers are most sensitive.

Control electronics receive commands through an input keypad for setting prescribed fluid dose to be delivered and such inputs are translated into signals to control the motor and pumping mechanism. Various safety devices feed back operational information to the control electronics, including detection of motor speed and motion of pump elements, air bubbles in the fluid path, drip rate, high pressure, low fluid, low/no flow, overtime, and the like. The present infusion device includes battery power for portability, and is housed in one RF shielded housing for convenient location anywhere within the MRI scan room without introducing image degrading RF interference or producing distortions of the homogeneous magnetic field, and without being affected by the strong magnetic fields or high-level RF energy produced by the MRI system. Such unrestricted placement of the device is of great importance to the safety and convenience of the attending MRI staff and imaging patient.

In an additional embodiment, a method is employed to substitute an MRI-compatible pumping device for a prior-connected, non-MRI-compatible pumping device while preserving the patient's connection to a prior-connected primary IV infusion set. The patient is commonly connected to a primary IV set, which is placed into a primary, non-MRI-compatible pump. Upon arrival at the MRI suite, a secondary, MRI-compatible pump will then be attached to a secondary IV set to continue actively-pumped IV fluid delivery. To employ the secondary pump, the primary pump is removed from the patient's installed IV set, thus activating a flow preventer (shutting off flow) that is standard on most IV sets. The fluid receiving end of the secondary IV set ("upstream" of the secondary pump) is connected to the upstream end of the primary set near the IV fluid container, for instance by puncturing a connector site on the primary set with a hollow needle on the secondary set, or via needless side connector. Air is flushed out by flowing fluid from the upstream container, and the fluid delivery end of the secondary IV set ("downstream" of the secondary pump) is connected to the downstream end of the primary set. Pumping of the fluid may then be resumed with the MRI-compatible pump, and the patient and MRI-compatible pump may then be moved close to the MRI scanner. One may simply disconnect and discard the secondary set so employed after the MRI procedure, and re-install the original primary set into the original, non-MRI-compatible pump while preserving the patient's connection to the primary IV set, in order to return the IV control to the original primary pumping device.

DETAILED DESCRIPTION OF THE INVENTION

Figure 1:
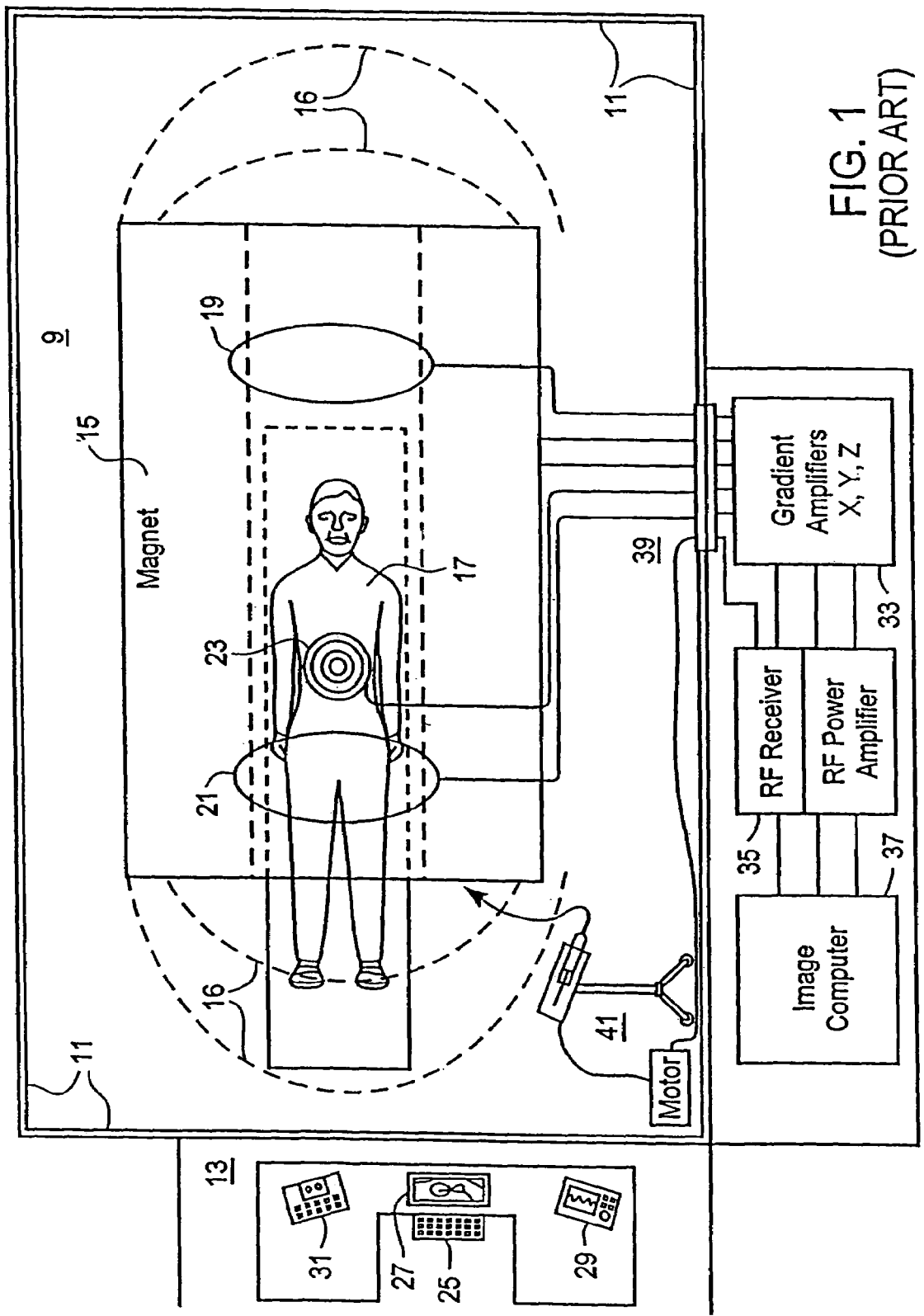
FIG. 1 is a pictorial plan view of a conventional MRI system showing typical placement of operational components.

Referring now to the plan view in FIG. 1 of an MRI system, the scanning room 9 is disposed within shielding boundary walls 11, with a control room 13 for operators or attendant personnel positioned outside the boundaries of the scanning room 9. The scanning room 9 includes the image acquisition equipment including a source 15 of intense magnetic field 16 that emanates from the source in substantially homogenous array throughout the adjacent space and around a patient 17. Various components of the system for performing the image acquisition operations, including gradient 19 and sensor 21 and RF coils 23 are disposed about the patient 17 for stimulating the nuclei 'echos' to map the positions thereof within the spatially-homogenous magnetic field 16 as the patient's body is scanned in conventional manner along multiple orthogonal axes. The shielding boundary walls 11 (and ceiling and floor) provide shielding against radio-frequency interference and, as fabricated with ferrous materials, may also establish outer limits of the magnetic field distribution around magnetic 15.

The control room 13 is disposed outside the shielding boundary walls 11 and is equipped with computer input keyboard 25, computer display 27, monitor 29 of patient's vital life signs, controls 31 for liquid infusion apparatus, and the like. Such representative equipment is housed outside the shielding boundary walls 11 to inhibit intrusion of spurious magnetic and electrostatic and RF signals into the image acquisition operations within the scanning room 9. Similarly, the gradient amplifiers 33 for amplifying signals from conventional gradient coils 19-21, along X, Y, and Z coordinates and RF amplifiers 35 and the image-processing computer 37 are also located outside the shielding boundary walls 11 for the same reason. The thru-wall interconnections 39 between the components within the scanning room 9 and the electronic equipment 25, 27, 29, 31, 33, 35, 37 disposed outside the room 9 typically also includes RF shielding to diminish the sources and the portals by which and through which RFI signals may enter the scanning room 9.

A liquid-injection device 41 commonly resides within the scanning room 9 to administer IV injection into the patient 17 of liquid compositions, for example, that enhance image acquisition (e.g., contrast medium) or that otherwise provide diagnostic or therapeutic benefits to the patient 17 being scanned. Such conventional injection device 41 should desirably be positioned close to the patient 17 to facilitate IV liquid infusion, but must be positioned remotely to avoid disrupting the homogeneous magnetic field 16, and to minimize RFI and operational failures of the infusion device 41 resulting from operating in the intense magnetic field adjacent the patient 17. Control of such infusion device 41 may be via remote controller 31 disposed within control room 13.

Figure 2:
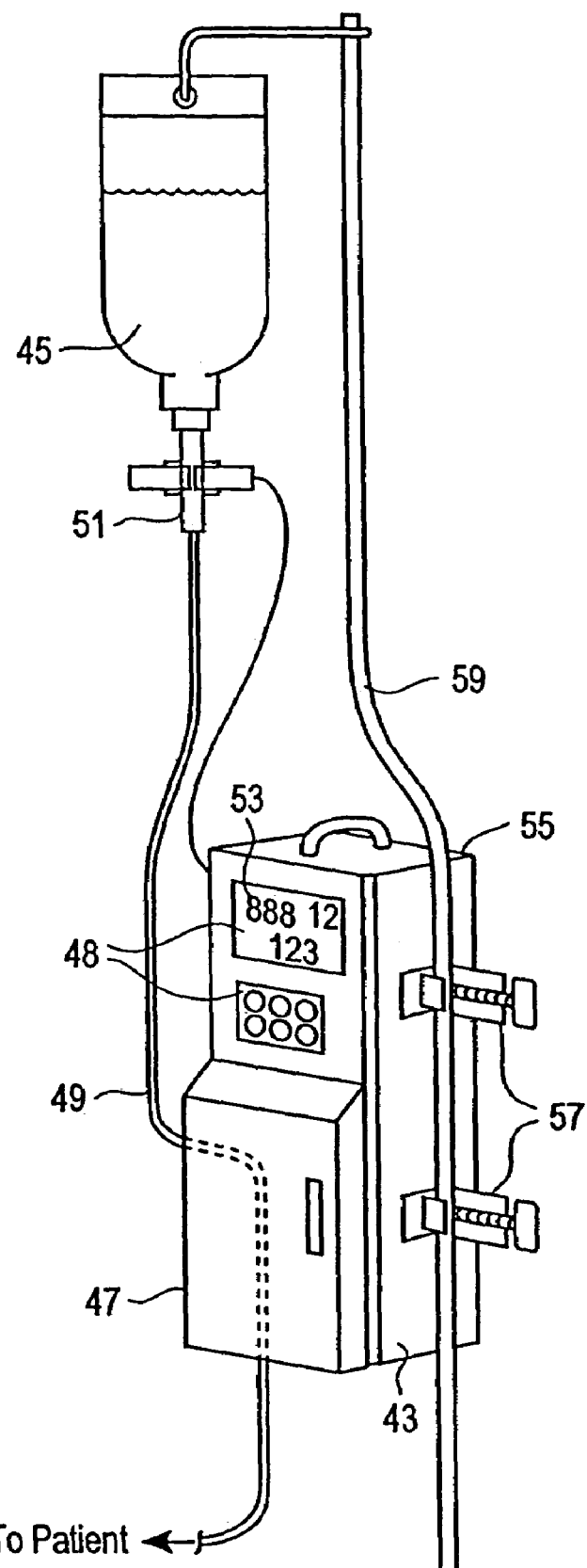
FIG. 2 is a partial perspective view of an infusion device in accordance with one embodiment of the present invention.

In accordance with the embodiment of the invention illustrated in FIG. 2, an improved liquid infusion device 43 is operable within intense magnetic fields and with negligible RFI to provide positive displacement of a liquid 45 such as saline or contrast medium, or sedative, or the like, in controlled volumes per unit time. The device does not include any ferrous, or magnetic materials, and is substantially shielded against irradiating any RFI during operation. Specifically, the device 43 includes a pump in the lower chamber 47, as later described herein. The pump chamber 47 receives therein the flexible, resilient tubing 49 that is pre-packaged and sterilized as a component of a conventional IV liquid infusion set that also includes a conventional drip chamber 51 as part of the infusion set. Controls for the pump in chamber 47 include an operator's input keypad 48 for setting infusion parameters, and a drip detector 53 that can be disposed above the drip chamber 51 to detect flow of liquid from the supply 45. A display 53 is positioned in the upper portion of the housing 55 which may be formed of non-magnetic, RF-shielding material such as conductively-coated plastic or aluminum, or the like. The housing 55 attaches with one or more clamps 57 to a rigid support 59 formed of non-magnetic material such as fiberglass or aluminum, or the like.

Figure 3:
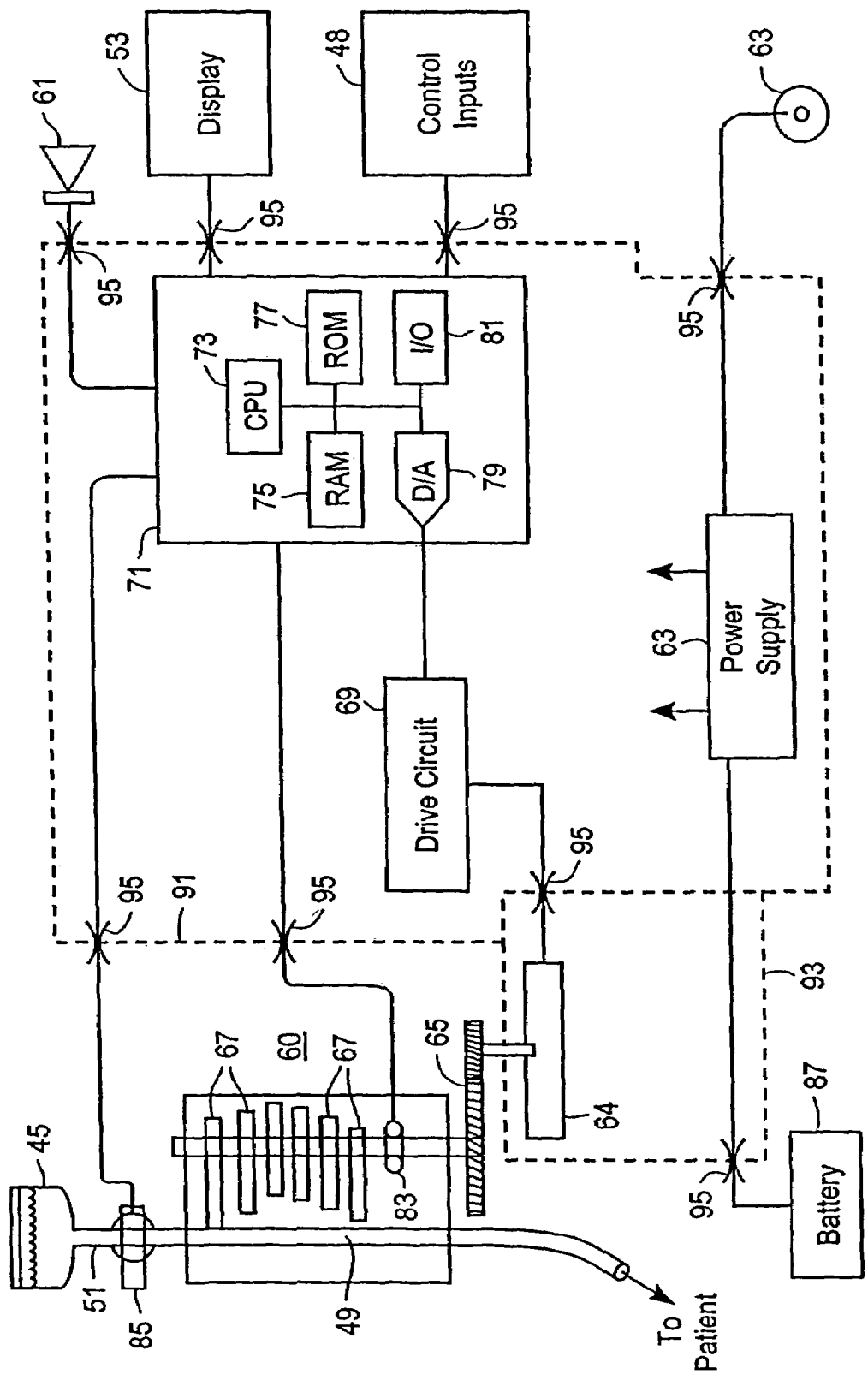
FIG. 3 is a block schematic diagram of the infusion device of FIG. 2.

Referring now to the pictorial block schematic diagram of FIG. 3, there is shown a peristaltic-type positive-displacement pump 60 disposed within the pump chamber 47 of the housing 55 to operate with the length of tubing 49 that passes therethrough between the drip chamber 51 and the patient. The peristaltic pump 60 (linear or rotational) is driven by an ultrasonic motor 64 via appropriate mechanical linkage 65 to actuate a squeeze roller against the tubing 49 in known peristaltic pumping manner, or to actuate a series of elements 67 through a linear tubing-squeezing sequence to produce peristaltic pumping action in known manner. Various visual and audible annunciators 61 may be provided to signal operational conditions either within acceptable limits, or within error or failure conditions.

A conventional ultrasonic driving motor 64 is powered in known manner by multiphasic signals applied thereto from the motor drive circuit 69. A controller 71 for the device includes a central processing unit 73 with associated peripheral components including Random Access Memory 75, Read-Only Memory 77, Digital-to-Analog converter 79, and an Input/Output channel 81. This controller 71 receives input control information from the operator's keypad 48, and receives feedback information about pump speed from sensor 83 and about liquid flow from drip detector 85 disposed about the drip chamber 51. In response to the inputs supplied thereto, the controller 71 operates on stored programs to actuate a display 53 of operating parameters (or other data), and to actuate the motor drive circuit 69 for energizing the ultrasonic motor 64 for rotation at a controlled speed. A power supply 63 is connected to the controller 71 and drive circuit 69 to supply electrical power thereto, and is connected to a battery 87 to receive electrical power therefrom during stand-alone operation, or to receive line voltage via plug 63, as required.

In accordance with this embodiment of the present invention, no magnetic material is used in any of the components of the infusion device 43 including the ultrasonic motor 64, pump 60, power supply 63, controller 71 and associated components. Additionally, none of such components is adversely affected during operation by a strong magnetic field. And, any RF energy that may be generated by electronic signals within the ultrasonic motor 64, drive circuit 69, controller 71, power supply 63 or associated components is specifically shielded by conductive structures 91, 93 disposed around such components to inhibit radiation of RFI. Additionally, radio-frequency interference filters 95 are disposed about all through-shield conductors to inhibit radiation of RFI through such portals.

Figure 4:
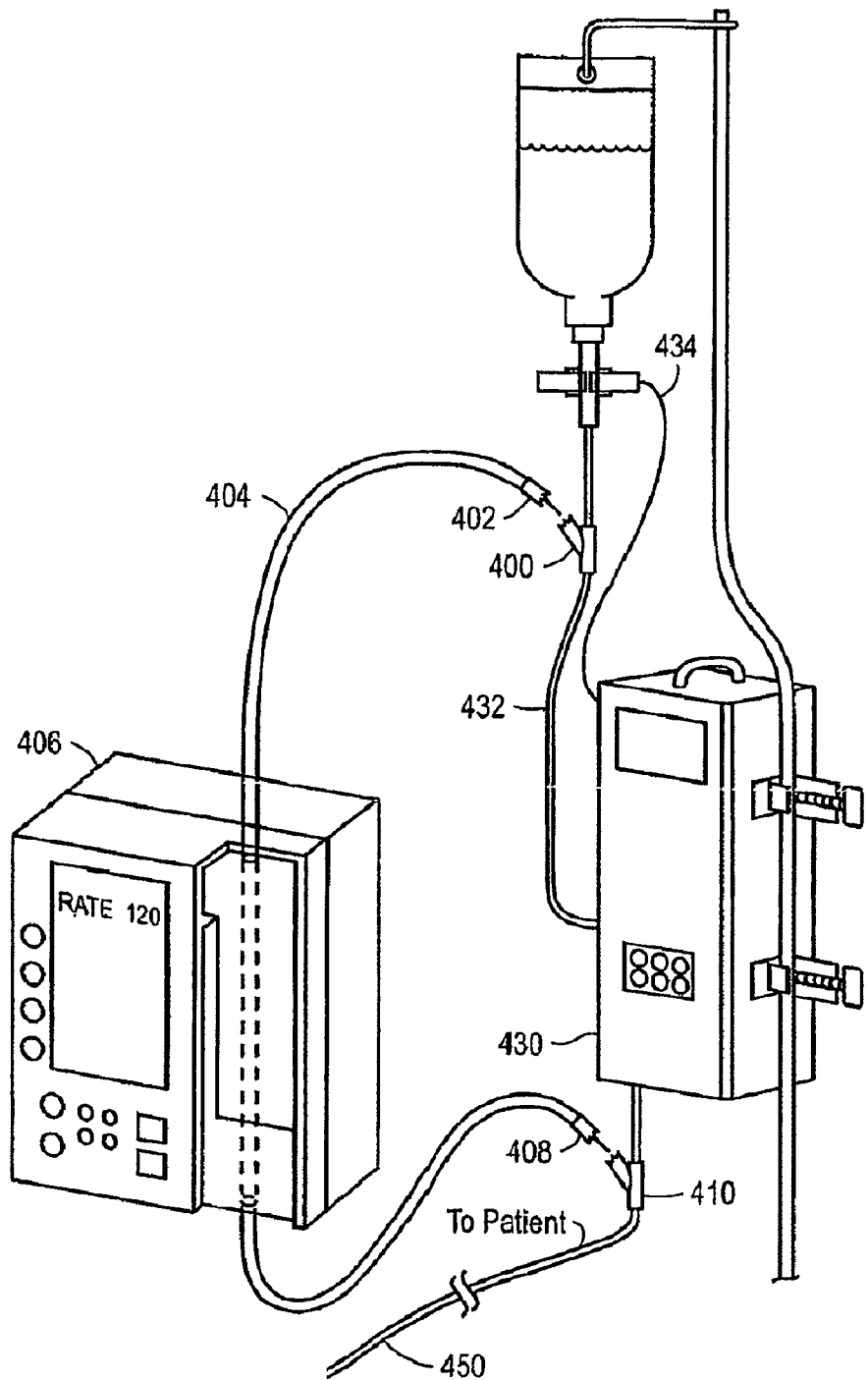
FIG. 4 is a partial perspective view of the two pumping apparatuses in accordance with one embodiment of the present pump-substitution invention.

Referring now to FIG. 4, in an additional embodiment of the present invention, a method is employed to substitute an MRI-compatible pumping device 406 for a prior-connected, non-MRI-compatible pumping device 430 while preserving the patient's 450 connection to a prior-connected primary IV infusion set 432. The patient 450 is initially connected to a primary IV infusion set 432, which is connected to a non-MRI-compatible primary pump 430. The primary pump 430 controls the pumping action in response to a sensor 434 that monitors liquid flow. Fluid connectors are disposed in the primary IV set upstream 400 and downstream 410 of the primary pump. Fluid connectors are also disposed in the secondary IV set upstream 402 and downstream 408 of the secondary pump 406.

Figure 5:
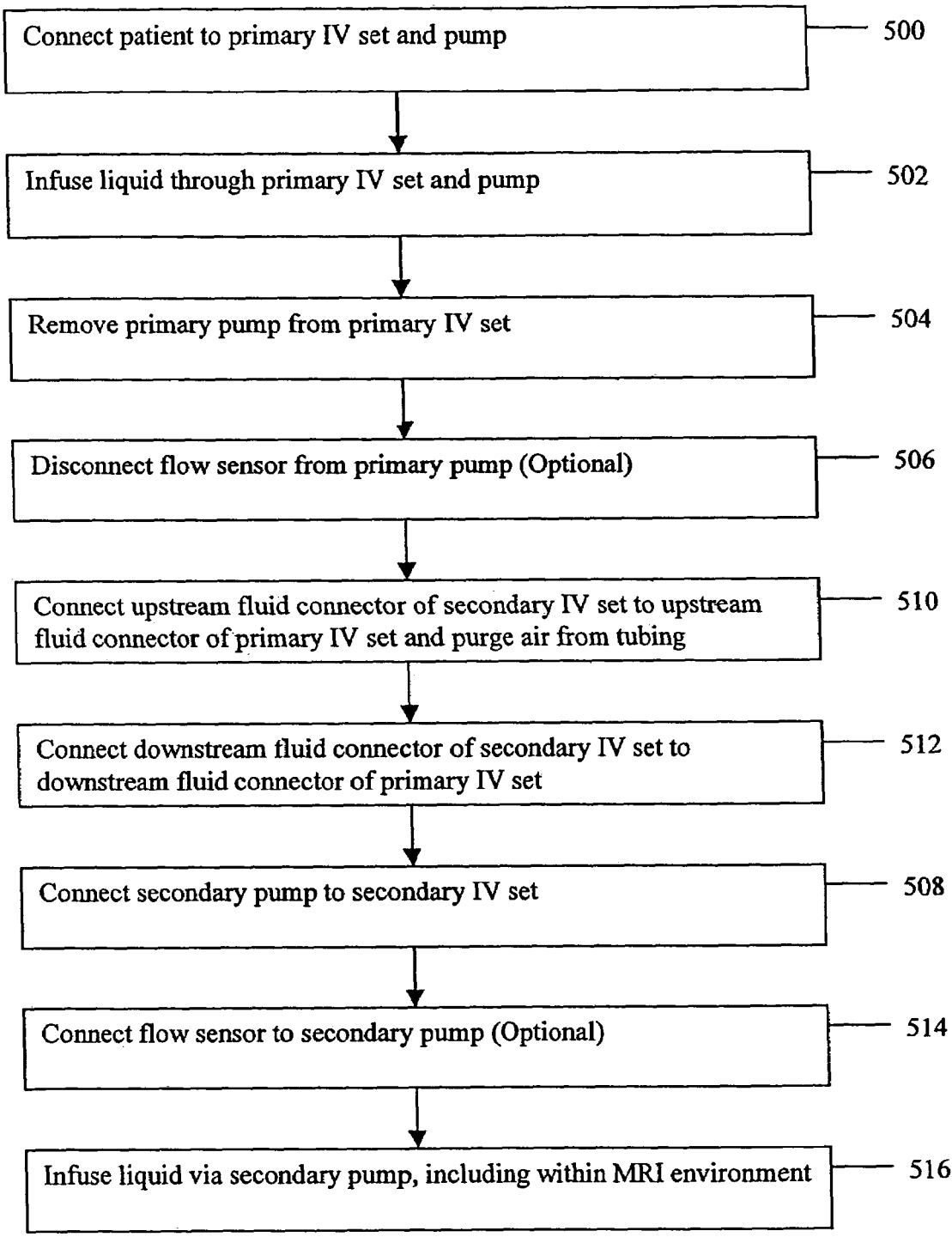
FIG. 5 is a flowchart illustrating a method of temporarily substituting a secondary IV pump for a primary IV pump without removing the patient's primary IV set in accordance with the present invention.

Referring now to the flowchart of FIG. 5, a method is illustrated for substituting an MRI-compatible pumping device 406 for a prior-connected, non-MRI-compatible pumping device 430 while preserving the patient's 450 connection to a prior-connected primary IV infusion set 432. Initially, the patient 450 is connected 500 to the primary IV set 432 and primary pump 430, and liquid is infused 502 into the patient 450 through the primary IV set 432 and primary pump 430. Before entry of the patient into the MRI environment, the primary pump 430 is removed 504 from the primary IV set 432 at a standard connector which then prevents the flow of liquid through the IV set via a shut-off mechanism upstream of the primary pump. In another embodiment, a flow sensor 434 connected between the liquid source and the primary pump is disconnected 506.

The secondary MRI-compatible pump 406 is connected 508 to a secondary IV set 404. The secondary pump 406 may include a sensor for monitoring liquid flow to control the pumping action.

To transition a patient 450 from a non-MRI-compatible pump 430 to an MRI-compatible pump 406 without altering the primary IV set 432 as installed on a patient 450, the upstream fluid connector 402 of the secondary IV set 404 is connected 510 to the upstream fluid connector 400 of the primary IV set 432. After purging the tubing of air, the downstream fluid connector 408 of the secondary IV set 404 is connected 512 to the downstream fluid connector 410 of the primary IV set 432. Then the secondary IV set is mounted 508 into the secondary (MRI-compatible) IV pump. In one embodiment, a sensor 434 may be connected 514 to the pump 406 for measuring the liquid pumped from the liquid source. Finally, liquid is infused 516 into the patient 450 through the installed primary IV set 432 and the secondary pump 406. Because the secondary pump 406 is MRI-compatible, the infusion may continue via the secondary pump within the MRI environment. The primary IV set 432 remains installed on a patient 450 who therefore does not have to be directly connected to the secondary IV set 404, but rather the secondary set "bypasses" the central (pumping) section of the primary set.

In an additional embodiment, the secondary pump 406 is connected to the primary IV set 432 before the primary pump 430 is removed from the primary IV set.

Figure 6:
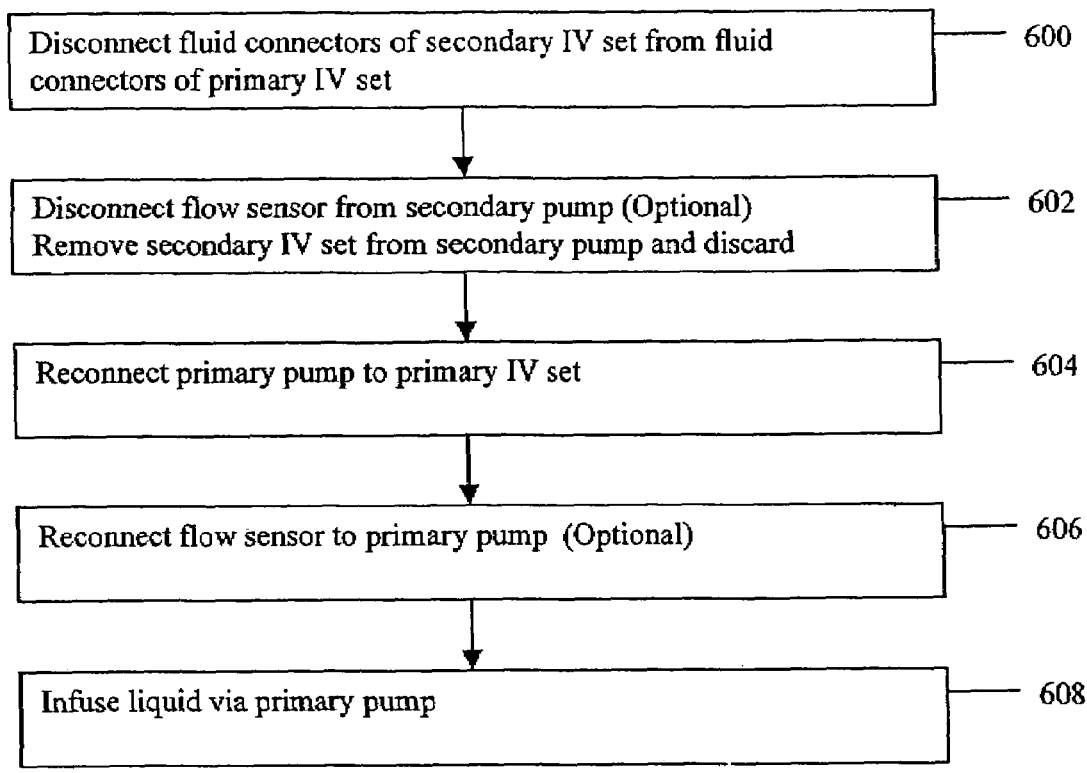
FIG. 6 is a flowchart illustrating a method of replacing a secondary IV pump with a primary pump in accordance with the present invention.

Referring now to the flowchart of FIG. 6, a method is illustrated for removing the secondary pump 406 and reconnecting the primary pump 430 after the patient 450 is removed from the MRI environment. The fluid connectors 402 and 408 of the secondary IV set 404 are disconnected 600 from the fluid connectors 400 and 410 of the primary IV set 432. This prevents flow of liquid through the secondary IV set. In one embodiment, the flow through the primary IV set 432 is prevented by a shut-off mechanism disposed in the primary IV set. In another embodiment, the user may manually cut off fluid via hand operated slide or roller clamp, or the like. The secondary IV set is removed 602 from the secondary pump and is discarded. The primary pump 430 is reattached or reconnected 604 to the primary IV set 432 and may be re-connected 606 to the flow sensor 434 to control the rate of liquid infusion through the primary IV set 432. Finally, liquid is again infused 608 into the patient 450 via the primary IV set 432, the primary pump 430, and the original attachment of the primary IV set to the patient.

Therefore, the liquid infusion device of the present invention is configured without magnetic materials for operation within intense magnetic fields to administer IV fusion of liquid to a patient in an MRI environment. The infusion device may be positioned close to a patient during image acquisition without significantly distorting the homogeneous magnetic field around an MRI scanner, and without emitting harmful RFI in the vicinity around a patient from whom extremely low-level RF 'echoes' are being detected during image acquisition. Such MRI-compatible infusion device may be conveniently substituted for a non-MRI-compatible infusion device without altering attachment to a patient of a primary infusion set, while also minimizing risk of breaking the sterility of the IV solution path.

What is claimed is:

1. A method of temporarily replacing with a secondary MRI-compatible pump a primary liquid-infusing pump coupled through a primary intravenous (IV) injection set between a liquid source and a patient while preserving the patient's connection to the primary IV set, the method comprising:

connecting the patient to the primary IV set, wherein tubing of the primary IV set is used with the primary liquid-infusing pump;

after connecting the patient to the primary IV set, infusing liquid into the patient through the primary IV set with the primary pump;

after infusing liquid into the patient through the primary IV set with the primary pump, inhibiting fluid flow through the primary IV set;

after infusing liquid into the patient through the primary IV set with the primary pump, connecting a secondary IV set to the primary IV set establishing fluid connections at locations upstream and downstream of the primary pump while preserving the patient's primary IV set connection to the liquid source, wherein tubing of the secondary IV set is used with the secondary pump; and after connecting the secondary IV set to the primary IV set, infusing liquid into the patient through the connection thereof to the primary IV set and through the secondary pump and secondary IV set.

2. The method of claim 1 for restoring liquid infusion into the patient through the primary pump, further comprising:

removing the fluid connections of the secondary IV set to the primary IV set and disabling the secondary pump; and enabling the primary IV set and the primary pump to infuse liquid into the patient through the primary IV set and the primary pump.

3. The method of claim 1 in which the secondary pump is MRI-compatible and is disposed within an MRI environment for infusing liquid in a patient within the MRI environment.

4. The method of claim 1, wherein the primary pump is disengaged from the primary IV set following connection thereto of the secondary IV set and secondary pump.

5. The method of claim 1, wherein the infusion of liquid through the secondary pump is controlled in response to liquid to be infused available from the liquid source.

6. The method of claim 2, wherein the flow of liquid through the primary IV set is enabled upon engagement of a shut-off mechanism by the primary pump.

7. The method of claim 1, wherein connecting a secondary IV set to the primary IV set at locations upstream and downstream of the primary pump occurs after infusing liquid into the patient though the primary IV set and the primary pump.

8. The method of claim 1, wherein connecting a secondary IV set to the primary IV set at locations upstream and downstream of the primary pump occurs without altering the patient's connection with the primary IV set.

9. A method of replacing a first liquid-infusing pump with a second MRI-compatible liquid infusing pump, comprising:
   stopping flow of liquid through a first set of IV tubing components used with the first liquid-infusing pump, wherein the first set of IV tubing components provides a conduit for fluid flow from an IV fluid container to a patient with a rate of fluid flow through the first set of IV tubing components controlled by the first liquid-infusing pump;
   connecting a second set of IV tubing components used with the second liquid-infusing pump to the first set of IV tubing components at locations upstream and downstream of the first liquid-infusing pump without disconnecting the first set of IV tubing components, so that the second set of IV tubing components provides a conduit for fluid flow that bypasses a pumping section of the first set of IV tubing components without breaking the first set of IV tubing's connection from the IV fluid container to the patient;
   after stopping flow of liquid through the first set of IV tubing components, disconnecting the first liquid-infusing pump from the first set of IV tubing components;
   after stopping flow of liquid through the first set of IV tubing components, connecting the second liquid-infusing pump with the second set of IV tubing components; and
   controlling flow of liquid through the second set of IV tubing components using the second liquid-infusing pump.

10. The method of claim 9, wherein stopping flow of liquid through the first set of IV tubing comprises preventing flow of liquid through the first set of IV tubing via a mechanism in the proximity of the first liquid-infusing pump.

11. The method of claim 9, further comprising:
   stopping flow of liquid through the second set of IV tubing components;
   controlling flow of liquid through the first set of IV tubing components using the first liquid-infusing pump after stopping flow of liquid through the second set of IV tubing components.

12. The method of claim 9, wherein the second liquid-infusing pump is engaged with the second set of IV tubing components after the first liquid-infusing pump is disengaged from the first set of IV tubing components.

13. The method of claim 9, wherein the first liquid-infusing pump is not compatible for use in an MRI environment, and the second liquid-infusing pump is compatible with use in an MRI environment.

\* \* \* \* \*